United States Patent [19]
Johnson

[11] Patent Number: 5,204,128
[45] Date of Patent: Apr. 20, 1993

[54] METHOD OF TREATING MINT OILS TO REDUCE PULEGONE AND MENTHOFURAN CONTENTS

[75] Inventor: Sonya S. Johnson, Brookfield, Ill.

[73] Assignee: Wm. Wrigley Jr. Company, Chicago, Ill.

[21] Appl. No.: 796,090

[22] Filed: Nov. 20, 1991

[51] Int. Cl.⁵ .................. A23L 1/222; A23G 3/30
[52] U.S. Cl. ........................ 426/3; 426/650; 426/651; 426/534; 426/533
[58] Field of Search .................... 426/3-6, 426/650, 651, 534, 533

[56] References Cited

U.S. PATENT DOCUMENTS

| | | | |
|---|---|---|---|
| 4,440,790 | 4/1984 | Blackwell et al. | 426/3 |
| 4,456,621 | 6/1984 | Blackwell et al. | 426/3 |
| 4,476,142 | 10/1984 | Netherwood et al. | 426/3 |
| 4,478,864 | 10/1984 | Blackwell et al. | 426/534 |
| 4,613,513 | 9/1986 | Hussein | 426/651 |
| 4,708,880 | 11/1987 | Hussein | 426/424 |
| 4,844,883 | 7/1989 | Patel | 426/3 |
| 4,861,616 | 8/1989 | Spencer | 426/651 |
| 4,948,595 | 8/1990 | Patel et al. | 426/3 |
| 5,116,625 | 5/1992 | Patel et al. | 426/3 |

*Primary Examiner*—Jeanette Hunter
*Attorney, Agent, or Firm*—Willian Brinks Olds Hofer Gilson & Lione

[57] ABSTRACT

A method of reducing the pulegone and menthofuran contents naturally present in mint oils comprising combining the mint oil with a Lewis acid, allowing the pulegone and menthofuran to react, neutralizing the mixture and separating the reaction products from the mint oil. This method also can be used with flavor oils naturally containing pulegone and no menthofuran, if a reactive diene is present in or added to the flavor oil. A method of preparing oral compositions, including chewing gum, comprising purified mint flavor is also provided. To chewing gum and other oral compositions is added mint flavor whose pulegone and/or menthofuran levels have been reduced by reacting with a Lewis acid, followed by neutralization and distillation.

20 Claims, 2 Drawing Sheets

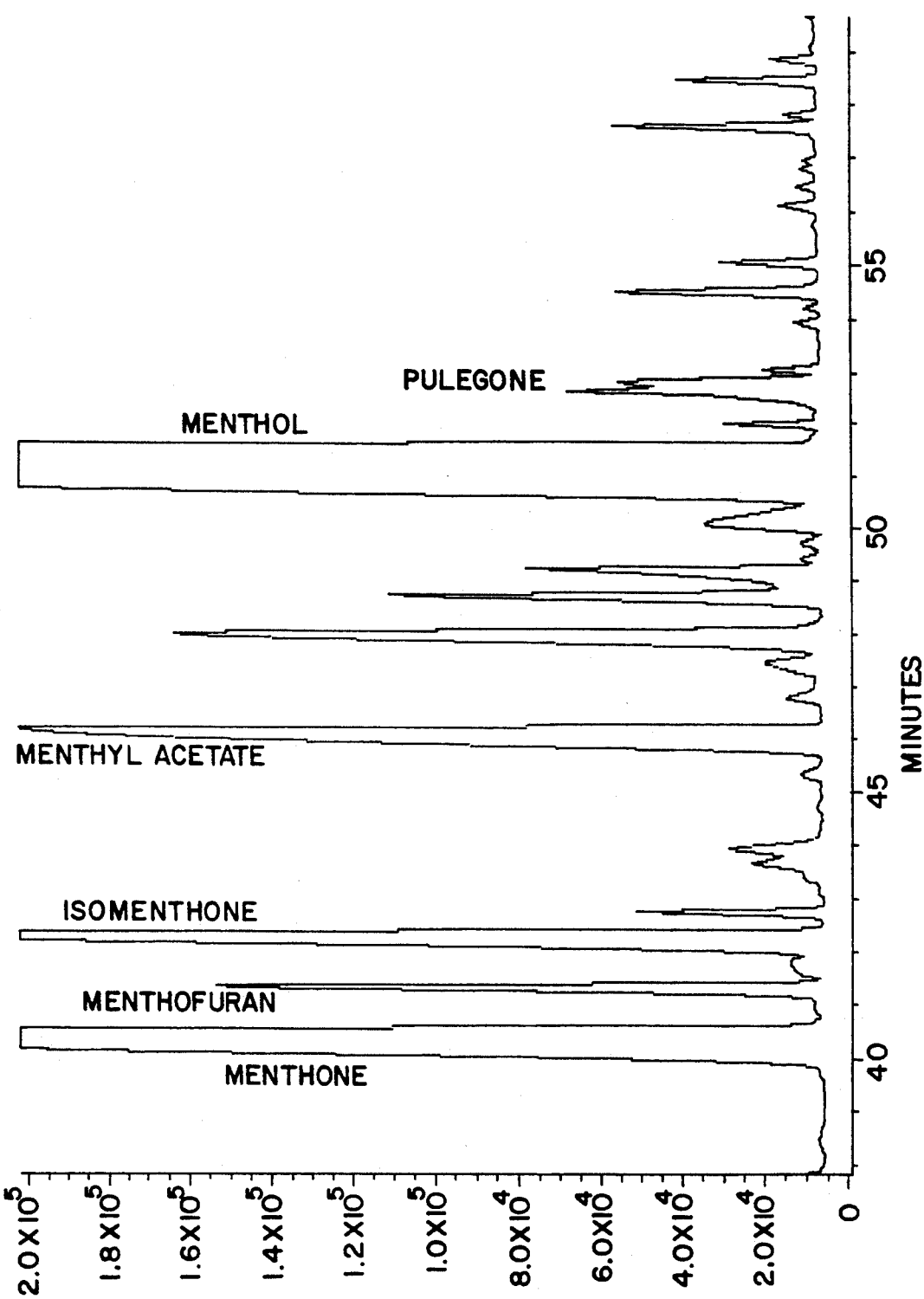

METHOD OF TREATING MINT OILS TO REDUCE PULEGONE AND MENTHOFURAN CONTENTS

BACKGROUND OF THE INVENTION

The present invention relates to a method of reducing the pulegone and menthofuran contents in mint oils, particularly peppermint oil. In addition, the present invention relates to a method of adding purified mint oil flavors to oral compositions, including chewing gum.

Mint oil flavors utilized in oral compositions naturally vary in their contents of pulegone and menthofuran. Recently, it has been recognized that pulegone is an undesirable component of mint oil flavors because it is a potential toxin. Menthofuran also is undesirable at moderate to high levels in mint oil flavors, because it can contribute dirty or diesel notes to the flavor, and it can readily oxidize to other undesirable compounds.

Pulegone is also known as 5-methyl-2-(1-methylethylidene)cyclo-hexanone, R-(+)-p-menth-4(8)-en-3-one and alternately as 1-methyl-4-isopropylidene-3-cyclohexanone. It has a molecular weight of 152.23 and the chemical structure shown below:

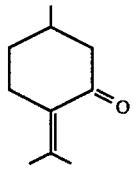

Pulegone is normally present as a liquid and is practically insoluble in water but is miscible in alcohol, ether and chloroform. The levels of pulegone are generally higher in less expensive peppermint oils, such as those obtained from *Mentha peperita* grown in the Yakima valley of Washington. Pulegone is also present in spearmint oil which is obtained from *Mentha spicata* and in corn mint oil which is obtained from *Mentha arvensis*.

Menthofuran is present in peppermint oil and is chemically known as 3,6-dimethyl-4,5,6,7-tetrahydrocoumarone. It has a molecular weight of 150.21 and has the chemical structure shown below:

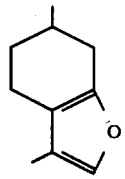

U.S. Pat. No. 4,861,616 to Spencer, issued Aug. 29, 1989, teaches a method of reducing the pulegone content of peppermint oil which stereospecifically hydrogenates pulegone and increases the menthone and menthol content of peppermint oil. Spencer also discloses enhanced stability against menthofuran oxidative breakdown.

U.S. Pat. No. 4,440,790 to Blackwell et al., issued Apr. 3, 1984, discloses a process of stabilizing peppermint oil, which relates to selectively forming a menthofuran-maleic anhydride adduct. No effect on pulegone content is mentioned, nor does there appear to be a change in the pulegone peaks in FIGS. 1 and 2 (before and after processing, respectively) of Blackwell et al.

What is needed is a method of conveniently removing both pulegone and menthofuran from mint oils without harming the flavor.

SUMMARY OF THE INVENTION

One embodiment of the present invention is a method of removing pulegone and menthofuran from mint oils, particularly peppermint oil. The method generally comprises mixing the peppermint oil with a Lewis acid and permitting the mixture to react. Then the reaction mixture is neutralized and the neutralized mixture is distilled to separate the peppermint oil flavor from the reacted pulegone and menthofuran.

Another embodiment of the present invention is a method of removing pulegone from mint oils, particularly spearmint oil and corn mint oil. The method generally comprises mixing a reactive diene such as menthofuran with the mint oil and then mixing that combination with a Lewis acid and permitting the mixture to react. Then, the reaction mixture is neutralized and the neutralized mixture is distilled to separate the spearmint oil or corn mint oil from the reacted pulegone.

Another embodiment of the present invention is a method of removing menthofuran from flavor oils. The method generally comprises mixing the flavor oil with a Lewis acid and permitting the mixture to react. Then, the reaction mixture is neutralized and the neutralized mixture is distilled to separate the flavor oil from the reacted menthofuran.

Another embodiment of the present invention is a method of adding mint oil flavors with reduced pulegone and/or menthofuran contents to oral compositions, including chewing gum.

A further embodiment of the present invention is a chewing gum composition comprising a mint flavor with reduced pulegone and/or menthofuran content.

The present invention is advantageous in that it reduces pulegone and menthofuran contents in mint oil flavors without adversely affecting the flavor. The elimination of these chemicals renders the oil less toxic and more acceptable sensorially, improving aroma and other flavor properties. These advantages are provided by a relatively simple, safe, and inexpensive method. In particular, the present invention can be carried out in a controlled fashion, using simple and inexpensive equipment. The present invention is also well suited for both small and large batch processing.

While not wishing to be bound by any theory, it is believed that menthofuran and pulegone in peppermint oil will, in the presence of a Lewis acid catalyst, undergo Diels-Alder reactions to produce high molecular weight products from which the rest of the peppermint oil is easily distilled. There are believed to be several ways in which such a reaction could proceed. Some of the proposed mechanisms are shown below.

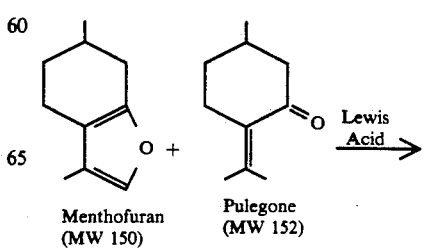

Menthofuran (MW 150) + Pulegone (MW 152) → Lewis Acid

-continued

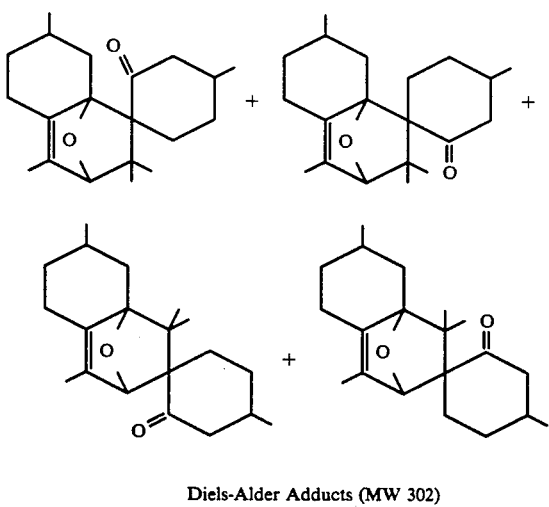

Diels-Alder Adducts (MW 302)

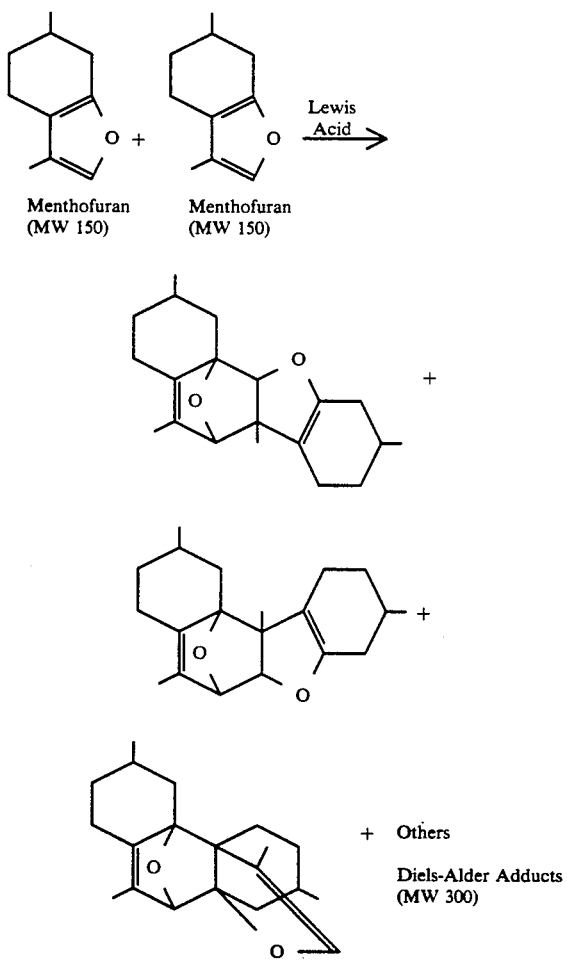

Diels-Alder Adducts (MW 300)

As the preceding diagrams indicate, menthofuran can react with itself and with pulegone. However, it is believed that pulegone cannot react with itself, because pulegone requires a reactive diene component which may be menthofuran or another mint component. Hence, this invention can be practiced on peppermint oil which naturally contains both pulegone and menthofuran. For spearmint and corn mint oil which naturally contain pulegone and lack menthofuran or other reactive diene, this invention calls for the initial addition of a reactive diene such as menthofuran to the flavor oil.

The possibility of other Diels-Alder reactions in this system, such as between menthofuran and other peppermint oil components, such as myrcene, has not been ruled out. However, the exact reactions are unimportant since the expected Diels-Alder adducts would always be high boiling compounds which are easily separated from the peppermint oil by distillation. Nevertheless, available data indicate that the undesirable peppermint components, pulegone and menthofuran, react readily while desirable peppermint compounds react little or not at all. Analysis by gas chromatography and mass spectroscopy has shown that no significant Diels Alder adducts are formed from peppermint oil other than menthofuran and pulegone adducts, and there is no significant loss of desirable oil components. It is fortuitous and surprising that no other active dienes or active dienophiles of significance exist in peppermint oil.

The above-described advantages of the present invention, as well as others, will become apparent from the following description which discloses presently preferred embodiments of the present invention.

BRIEF DESCRIPTION OF THE DRAWINGS

FIG. 2 represents a gas chromatography analysis of a Yakima peppermint oil treated according to the invention as described in Example 1.

DETAILED DESCRIPTION OF THE PREFERRED EMBODIMENTS

Figure 1:
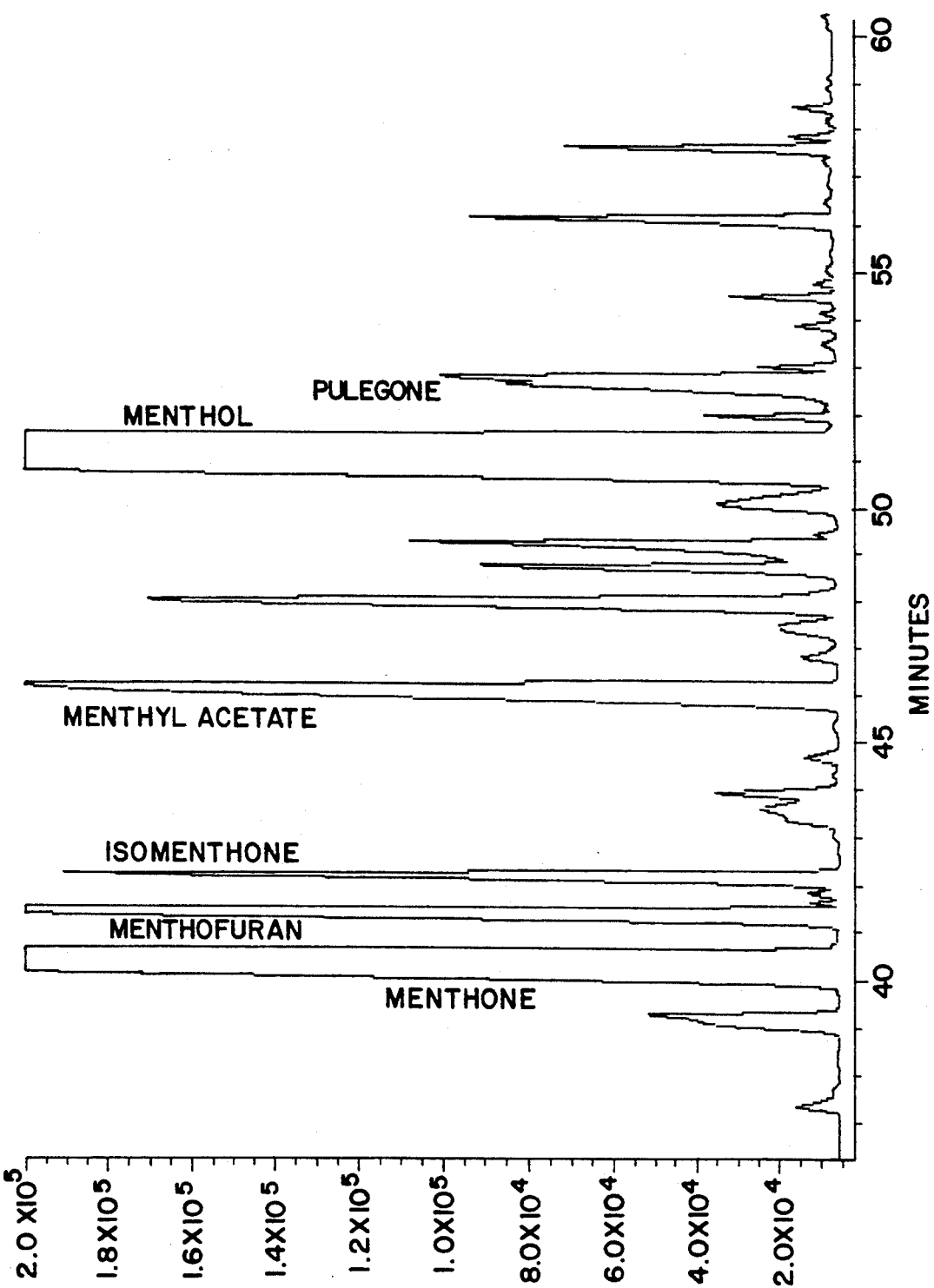
FIG. 1 represents a gas chromatography analysis of a Yakima peppermint oil before undergoing the inventive method.

The present invention is a method for treating mint oil to reduce the levels of pulegone and menthofuran. In summary, the method involves refluxing a mint oil in the presence of a Lewis acid, neutralizing the reaction mixture and then distilling the neutralized mixture to separate the relatively low boiling peppermint oil components from the higher boiling reaction products which are formed. The resulting distillation product exhibits reduced pulegone and menthofuran levels with minimal changes to other components.

In a preferred embodiment, the mint oil is peppermint oil. The amount of mint oil purified will vary, depending on the size of the reaction container available. In another embodiment, the mint oil is spearmint or corn mint oil. Because these mint oils naturally contain only pulegone and no significant amount of menthofuran, menthofuran or another reactive diene is added prior to the steps discussed below. A reactive diene is defined as a diene which will form Diels-Alder adducts with pulegone in the presence of a Lewis acid catalyst. Sufficient reactive diene is added to complex with the pulegone and thus lower the level of the pulegone, with minimal changes to other components.

The mint oil is mixed with a Lewis acid. A Lewis acid is a chemical species which has a vacant orbital which can accept an electron pair from a donor to form a covalent bond. Preferably, the Lewis acid is hydrochloric acid (HCl). Others which may be used include boron trifluoride ($BF_3$), boron trifluoride etherate ($BF_3C_2H_5$), aluminum trichloride ($AlCl_3$), $SnCl_4$, $SO_3$, $AlH_3$ and $Al(CH_3)_3$. Still other Lewis acids are known to those of ordinary skill in the art.

The Lewis acid catalyst is added in an amount sufficient to catalyze the reaction at a desired rate. Where hydrochloric acid is used as a catalyst, an appropriate level is about 10 ml of concentrated hydrochloric acid (12N) per kilogram of peppermint oil, although a wide range of levels is believed to be effective. Preferably, the Lewis acid is added in an amount of 0.01-1.0 moles per kilogram of mint oil. More preferably, the Lewis acid is added in an amount of 0.05-0.5 moles per kilogram of mint oil. Most preferably, the Lewis acid is added in an amount of about 0.1 mole per kilogram of mint oil.

Preferably, the mixture is permitted to react for several hours. The reaction should be allowed to proceed for at least one half hour. More preferably, the reaction should be permitted to proceed for at least 3 hours. Even more preferably, the reaction should proceed until the desired reduction in menthofuran and/or pulegone is achieved. The length of time required to react the flavor will vary and will depend upon various factors. These factors include but are not limited to the initial concentration of pulegone and menthofuran in the mint flavor, the desired degree of reduction of the two components, concentration of the Lewis acid, the batch size of mint flavor, and reaction temperature. All these factors affecting reaction time will be apparent to those skilled in the art.

The temperature of the reaction should be monitored and controlled. Preferably, the temperature should not be allowed to exceed 100° C. Even more preferably, the temperature should be maintained in the range of 40-80° C. at atmospheric pressure.

The reaction mixture is neutralized by adding alkali to the reaction mixture. Preferably, sodium hydroxide is used. Most preferably, sodium hydroxide is added in an amount in excess of the theoretical amount needed to neutralize the Lewis acid.

Next, the neutralized oil can be dried with sodium sulfate ($Na_2SO_4$) or by other appropriate means.

The oil is then filtered to remove the hydrated sodium sulfate if it has been used.

Then the oil is distilled, preferably under vacuum with heating to maintain a steady boil. Preferably, the distillation is continued until about 95% of the oil has distilled over. At 1 mm Hg, the distillation proceeds for about four hours and reaches a temperature of about 74° C. The distillate is purified mint oil. The residue contains the Diels-Alder adducts of pulegone and/or menthofuran.

The distilled mint oil is then ready for incorporation into oral compositions as a flavor. Preferably, the purified mint flavor is added to a chewing gum formulation. The purified flavor is generally added to the gum formulation late in the mixing process. Optimum levels of purified mint flavor may vary from about 0.1% to about 5% in a chewing gum formulation. Preferably, the level of flavor added is about 0.5% to about 1.5%.

In general, a chewing gum comprises a water-soluble bulk portion, a water-insoluble chewable gum base portion and typically, water-insoluble flavor ingredients. The water-soluble portion dissipates with a portion of the flavor over time during chewing. The gum base portion is retained in the mouth throughout the chew.

The insoluble gum base generally comprises elastomers, resins, fats and oils, waxes, softeners and inorganic fillers. Elastomers may include polyisobutylene, isobutylene-isoprene copolymer, styrene butadiene rubber, as well as natural latexes such as chicle. Resins include polyvinyl acetate and terpene resins. Fats and oils may also be included in the gum base including tallow, hydrogenated and partially hydrogenated vegetable oils and cocoa butter. Commonly employed waxes include paraffin, microcrystalline wax, and natural waxes such as beeswax and carnauba. The insoluble gum base constitutes about 5% to about 95% of the gum, and more preferably, about 20% to about 30%.

The gum base typically also includes a filler component. The filler component may be calcium carbonate, magnesium carbonate, talc, dicalcium phosphate, and the like. The filler may constitute about 5% to about 60% of the gum base. Preferably, the filler comprises about 5% to about 50% of the chewing gum base. The gum base also contains softeners, including glycerol monostearate and glycerol triacetate. Further, gum bases may also contain additional ingredients such as anti-oxidants, colors, and emulsifiers. The present invention contemplates using any commercially acceptable gum base.

The water-soluble portion of chewing gum may further comprise softeners, sweeteners, and flavors and combinations thereof. The softeners are added to the chewing gum in order to optimize the chewing ability and mouth feel of the gum. Softeners, also known in the art as plasticizers, generally constitute about 0.1% to about 15% of the chewing gum. Softeners contemplated by the present invention include glycerin, lecithin and combinations thereof. Aqueous sweetener solutions such as those containing sorbitol, hydrogenated starch hydrolysates, corn syrup, and combinations thereof may be used as softeners and binding agents in gum.

Sweeteners contemplated by the present invention for use in chewing gum include both sugar and sugarless components. Sugar sweeteners generally include saccharide-containing components commonly known in the art and include, but are not limited to, sucrose, dextrose, maltose, dextrin, dried invert sugar, fructose, levulose, galactose, corn syrup solids and the like, alone or in any combination. Sugarless sweeteners include components with sweetening characteristics but are devoid of the commonly known sugars and comprise, but are not limited to, sugar alcohols such as sorbitol, mannitol, xylitol, hydrogenated starch hydrolysates, maltitol, and the like, alone, or in any combination. Also contemplated for direct addition to the gum are high intensity sweeteners such as aspartame, Sucralose®, cyclamate, acesulfame-K, dihydrochalones, alitame, and saccharin.

Those persons skilled in the art will recognize that any combination of sugar or sugarless sweeteners may be employed in the chewing gum. Further, those skilled in the art will recognize a sweetener may be present in a chewing gum in whole or in part as a water-soluble bulking agent, and that the softener may be combined with a sweetener such as an aqueous sweetener solution.

The purified mint flavor may be added to the chewing gum in an amount from about 0.1% to about 5% and preferably from about 0.5% to about 1.5% of the gum. Flavors contemplated by the present invention include mint flavors such as peppermint oil, corn mint oil and spearmint oil. The purified mint flavor may be blended with other flavors such as essential oils, synthetic flavors, or mixtures thereof, including but not limited to, oils derived from plants and fruits such as citrus oils, fruit essences, clove oil, anise, and the like. Artificial flavoring components are also contemplated. Those skilled in the art will recognize that natural and artificial flavoring agents may be combined in any sensorially acceptable blend. All such flavors and flavor blends are contemplated by the present invention.

Ingredients such as colors, emulsifiers, and pharmaceutical agents may be added to the chewing gum.

In general, chewing gum is manufactured by sequentially adding the various chewing gum ingredients to any commercially available mixer known in the art. After the ingredients have been thoroughly mixed, the gum mass is discharged from the mixer and shaped into the desired forms such as by rolling into sheets and cutting into sticks, extruding into chunks, or casting into pellets. Generally, the ingredients are mixed by first melting the gum base and adding it to the running mixer. The base may also be melted in the mixer itself. Color may also be added at this time. A softener such as glycerin may then be added next along with the syrup and a portion of the bulking agent. Further portions of the bulking agents may be added to the mixer. Preferably, the purified mint oil flavor ingredients are added to the gum mixture near the end of the mixing process. The entire mixing procedure takes from about 5 minutes to 15 minutes; however, longer mixing times may be required. Those persons skilled in the art will recognize that many variations of the above-described procedure may be followed.

In another embodiment of the present invention, the purified mint oil flavor may be added to oral compositions such as mouthwash, toothpaste, pressed mints, hard candies (both sugar and sugarless), and beverages. Preferably, the purified mint oil flavor constitutes from about 0.01% to about 2% of the oral composition.

EXAMPLE 1

Removal of Pulegone and Menthofuran from Peppermint Oil

Approximately 200 g of "Prime Natural" Yakima peppermint oil (A. M. Todd Company, Kalamazoo, Mich., U.S.A.) was added to a 1000 ml two-neck round bottom flask. Then 2.00 ml of concentrated HCl (12N) was added along with a magnetic stir bar. The flask was placed in a mantle, and a condenser was attached with coolant circulating at 10° C. A 100° C. thermometer was inserted in the flask to monitor the mixture temperature. The apparatus was adjusted to maintain a 60° C. temperature to reflux the reaction mixture. Small samples of the reacting peppermint oil were withdrawn for analysis at the start (0 hours) and at 1, 2, 3, 4 and 5 hours thereafter. After five hours, the mixture was transferred to a flask for storage.

The samples of reacting peppermint oil were analyzed for pulegone and menthofuran by GC/MS. A 60 m fused silica, open tubular, capillary column (OV-1 type methyl silica) was used. A one microliter injection was split 80:1. An initial temperature of 70° C. was maintained for three minutes; then the temperature was increased at the rate of 3° per minute to 220° C., at which it was held. The results are shown below in Table 1.

TABLE 1

| Time (hrs.) | Menthofuran (%) | Pulegone (%) |
|---|---|---|
| 0 | 4.60 | 3.12 |
| 1 | 2.96 | 2.26 |
| 2 | 2.84 | 2.39 |
| 3 | 2.62 | 2.15 |
| 4 | 2.41 | 2.03 |

TABLE 1-continued

| Time (hrs.) | Menthofuran (%) | Pulegone (%) |
|---|---|---|
| 5 | 2.26 | 2.21 |

The data indicate that pulegone and menthofuran were reduced by 29% and 51% respectively, after five hours reaction. The reduced menthofuran level in this purified peppermint oil compares favorably with several more expensive, high quality peppermint oils which contain 2.00 to 2.70% menthofuran.

Next, the reaction mixture was neutralized by the addition of 1 gram of sodium hydroxide in water. This was mixed for about 30 minutes. Next, water was removed, first by physical separation and then by drying with sodium sulfate ($Na_2SO_4$). Then the oil was filtered to remove the hydrated sodium sulfate.

The filtered oil was distilled. The oil was placed in a 250 ml round bottom flask with a stir bar. The flask was then placed in a heating mantle, and connected to a vacuum distillation head. Stirring was initiated and a relative vacuum (absolute pressure of about 0.6 to 1.0 mm Hg) was established by connection to a vacuum pump. Gradually the mixture was heated. Distillation started at room temperature. Gradually the temperature increased to 74° C. after four hours. Approximately 110 ml of purified peppermint oil was distilled over in this process, a yield of about 55%.

The purified oil was then stored in an air-tight container and refrigerated until needed for blending into a food composition.

EXAMPLE 2

Preparing a Chewing Gum Containing a Treated Mint Flavor

The purified peppermint oil described in Example 1 may be included in a chewing gum formulation such as that described below:

| Ingredient | % by Weight |
|---|---|
| Sugar | 54.3 |
| Base | 20.0 |
| Corn Syrup | 13.0 |
| Glycerin | 2.0 |
| Purified Peppermint Flavor | 0.7 |
| Dextrose | 10.0 |
| | 100.0% |

The amount of purified mint flavor added to a chewing gum formulation may vary. The precise chewing gum formulation employed is not critical to the present invention.

In summary, a relatively simple and inexpensive method has been described for reducing the pulegone and/or menthofuran contents in mint oils. Although specific embodiments and examples have been described herein, it should be borne in mind that these have been provided by way of explanation and illustration and that the present invention is not limited thereby. Modifications which are within the ordinary skill in the art to make are considered to lie within the scope of the invention as defined by the following claims, including all equivalents.

We claim:

1. A method of reducing the pulegone and menthofuran contents of mint oil, comprising:

(a) mixing mint oil containing pulegone and menthofuran with a Lewis acid, to form a reaction mixture;
(b) maintaining the reaction mixture at a temperature below 100° C. for at least one half hour, thereby permitting the reaction mixture to form Diels-Alder adducts of pulegone and menthofuran, and to reduce the pulegone and menthofuran contents in the reaction mixture;
(c) neutralizing the reaction mixture after at least one half hour of reaction; and
(d) separating mint oil having reduced pulegone and menthofuran contents from the Diels-Alder adducts of pulegone and menthofuran.

2. The method of claim 1, wherein the mint oil is peppermint oil.

3. The method of claim 1, wherein the Lewis acid is hydrochloric acid.

4. The method of claim 1, wherein the separation step comprises distillation for a sufficient time and at sufficient temperature and vacuum to distill mint oil having reduced pulegone and menthofuran contents from the Diels-Alder adducts of pulegone and menthofuran.

5. A method of reducing pulegone content in a flavor oil, comprising:
(a) adding a reactive diene to a pulegone-containing flavor oil;
(b) mixing a Lewis acid with the flavor oil containing pulegone and the reactive diene, to form a reaction mixture;
(c) maintaining the reaction mixture at a temperature below 100° C. for at least one half hour, thereby permitting the reaction mixture to form Diels-Alder adducts of the reactive diene and the pulegone, and to reduce the pulegone content in the reaction mixture;
(d) neutralizing the reaction mixture after at least one half hour of reaction; and
(e) separating flavor oil having reduced pulegone content from the Diels-Alder adducts of the reactive diene and the pulegone.

6. The method of claim 5, wherein the flavor oil is spearmint oil.

7. The method of claim 5, wherein the flavor oil is corn mint oil.

8. The method of claim 5, wherein the Lewis acid is hydrochloric acid.

9. A method of reducing menthofuran content in a flavor oil, comprising:
(a) mixing a Lewis acid with flavor oil containing menthofuran, to form a reaction mixture;
(b) maintaining the reaction mixture at a temperature below 100° C. for at least one half hour, thereby permitting the reaction mixture to form Diels-Alder adducts of menthofuran with itself and to reduce the menthofuran content in the reaction mixture;
(c) neutralizing the reaction mixture after at least one half hour of reaction; and
(d) distilling the neutralized reaction mixture for sufficient time at sufficient temperature to separate the flavor oil having reduced menthofuran content from the Diels-Alder adducts.

10. The method of claim 9, wherein the Lewis acid is hydrochloric acid.

11. A method of reducing the pulegone content of a flavor oil which naturally contains a reactive diene, comprising:
(a) mixing flavor oil containing pulegone and a reactive diene with a Lewis acid, to form a reaction mixture;
(b) maintaining the reaction mixture at a temperature below 100° C. for at least one half hour, thereby permitting the reaction mixture to form Diels-Alder adducts of pulegone and the reactive diene and to reduce the pulegone and the diene contents in the reaction mixture;
(c) neutralizing the reaction mixture after at least one half hour of reaction; and
(d) separating flavor oil having reduced pulegone content from the Diels-Alder adducts.

12. The method of claim 11, wherein the Lewis acid is hydrochloric acid.

13. The method of claim 11, wherein the separation step comprises distillation for a sufficient time and at sufficient temperature and vacuum to distill flavor oil having reduced pulegone content from the Diels-Alder adducts.

14. A method of preparing a chewing gum containing mint flavor with reduced pulegone and menthofuran contents, comprising:
(a) combining mint oil comprising menthofuran and pulegone with a Lewis acid, to form a reaction mixture;
(b) maintaining the reaction mixture at a temperature below 100° C. for at least one half hour, thereby permitting the Lewis acid to react with the menthofuran and pulegone components in the mint oil to produce Diels-Alder adducts of menthofuran and pulegone;
(c) neutralizing the reaction mixture after at least one half hour of reaction;
(d) separating mint oil having reduced pulegone and menthofuran contents from the Diels-Alder adducts; and
(e) mixing the separated mint oil having reduced pulegone and menthofuran contents with chewing gum ingredients,
the mint oil constituting from about 0.1% to about 5% by weight of the chewing gum.

15. The method of claim 14, wherein the mint oil constitutes from about 0.5% to about 1.5% by weight of the chewing gum.

16. The method of claim 14, wherein the mint oil is peppermint oil.

17. A method of preparing a chewing gum containing spearmint flavor with reduced pulegone content, comprising:
(a) combining spearmint oil containing pulegone with a reactive diene to form a mixture of spearmint oil containing pulegone and reactive diene;
(b) combining the mixture of spearmint oil containing pulegone and reactive diene with a Lewis acid, to form a reaction mixture;
(c) maintaining the reaction mixture at a temperature below 100° C. for at least one half hour, thereby permitting the Lewis acid to react with the diene and pulegone components in the mixture of spearmint oil containing pulegone and reactive diene, to form Diels-Alder adducts of diene and pulegone;
(d) neutralizing the reaction mixture after at least one half hour of reaction;
(e) separating spearmint oil having reduced pulegone content from the Diels-Alder adducts; and
(f) mixing the spearmint oil having reduced pulegone content with chewing gum ingredients, the spearmint oil having reduced pulegone content constituting from about 0.1% to about 5% by weight of the chewing gum.

18. The method of claim 17, wherein the spearmint oil constitutes from about 0.5% to about 1.5% by weight of the chewing gum.

19. A chewing gum composition comprising mint oil having reduced menthofuran and pulegone contents, the mint oil having had its menthofuran and pulegone contents reduced by:
    (a) combining mint oil containing pulegone and menthofuran with a Lewis acid, to form a reaction mixture;
    (b) maintaining the reaction mixture at a temperature below 100° C. for at least one half hour, thereby allowing the menthofuran and pulegone components of the mint oil to form Diels-Alder adducts of menthofuran and pulegone;
    (c) neutralizing the reaction mixture after at least one half hour of reaction; and
    (d) distilling the reaction mixture to separate mint oil having reduced menthofuran and pulegone contents from the menthofuran and pulegone Diels-Alder adducts;
    the mint oil having reduced menthofuran and pulegone contents constituting from about 0.1% to about 5% by weight of the chewing gum.

20. An oral composition comprising mint oil having reduced pulegone content, the mint oil having had its pulegone content reduced by:
    (a) combining mint oil containing pulegone with a reactive diene and a Lewis acid, to form a reaction mixture;
    (b) maintaining the reaction mixture at a temperature below 100° C. for at least one half hour, thereby allowing the contained pulegone and reactive diene to form pulegone Diels-Alder adducts;
    (c) neutralizing the reaction mixture after at least one half hour of reaction; and
    (d) distilling the reaction mixture to separate mint oil having reduced pulegone content from the pulegone Diels-Alder adducts;
    the mint oil having reduced pulegone content constituting from about 0.01% to about 2% by weight of the oral composition.

* * * * *